US008617366B2

(12) United States Patent
Winarta et al.

(10) Patent No.: US 8,617,366 B2
(45) Date of Patent: Dec. 31, 2013

(54) DISPOSABLE UREA SENSOR AND SYSTEM FOR DETERMINING CREATININE AND UREA NITROGEN-TO-CREATININE RATIO IN A SINGLE DEVICE

(75) Inventors: Handani Winarta, Nashua, NH (US); Jianhong Pei, Boxborough, MA (US); Mary Lauro, Billerica, MA (US); Chung Chang Young, Weston, MA (US); Xiaohua Cai, Needham, MA (US)

(73) Assignee: Nova Biomedical Corporation, Waltham, MA (US)

( * ) Notice: Subject to any disclaimer, the term of this patent is extended or adjusted under 35 U.S.C. 154(b) by 1228 days.

(21) Appl. No.: 11/164,935

(22) Filed: Dec. 12, 2005

(65) Prior Publication Data

US 2007/0131548 A1 Jun. 14, 2007

(51) Int. Cl.
*G01N 33/487* (2006.01)
(52) U.S. Cl.
USPC ............ 204/403.01; 204/403.02; 204/403.03; 204/403.05; 205/777.5; 205/782
(58) Field of Classification Search
USPC .............. 204/403.01–403.15; 205/777.5–781
See application file for complete search history.

(56) References Cited

U.S. PATENT DOCUMENTS

| 3,930,957 A | 1/1976 | Cummings et al. |
| 4,225,410 A | 9/1980 | Pace |
| 4,244,787 A | 1/1981 | Klein et al. |
| 4,452,682 A | 6/1984 | Takata et al. |
| 4,476,005 A | 10/1984 | Tokinaga et al. |
| 4,505,784 A | 3/1985 | Mund et al. |
| 4,608,335 A | 8/1986 | Fossati |
| 4,713,165 A | 12/1987 | Conover et al. |
| 5,053,225 A | 10/1991 | Miyasaka et al. |
| 5,063,081 A | 11/1991 | Cozzette et al. |
| 5,194,133 A * | 3/1993 | Clark et al. .................. 204/608 |
| 5,236,567 A * | 8/1993 | Nanba et al. ............. 204/403.1 |
| 5,308,315 A | 5/1994 | Khuri et al. |
| 5,466,575 A | 11/1995 | Cozzette et al. |
| 5,518,623 A | 5/1996 | Keshaviah et al. |
| 5,575,895 A * | 11/1996 | Ikeda et al. ............. 204/403.1 |
| 5,698,083 A | 12/1997 | Glass |

(Continued)

FOREIGN PATENT DOCUMENTS

| EP | 0 142 130 B1 | 6/1991 |
| EP | 0 504 772 A2 | 9/1992 |

OTHER PUBLICATIONS

S.B. Adeloju, S.J. Shaw, G.G. Wallace, Pulsed-amperometric Detection of Urea in Blood Samples on a Conducting Polypyrrole-urease Biosensor, 1997, Analytica Chimica Acta, 341, pp. 155-160.*

(Continued)

*Primary Examiner* — Bach Dinh
(74) *Attorney, Agent, or Firm* — Robert R. Deleault, Esq.; Mesmer & Deleault, PLLC

(57) ABSTRACT

A disposable urea sensor has a laminated body having a fluid sample inlet end and an electrical contact end, a fluid sample inlet, a substantially flat sample chamber in communication between the fluid sample inlet and a vent opening, the sample chamber being adapted to collect a fluid sample through the fluid sample inlet, a working electrode and a reference electrode within the sample chamber, and a reagent matrix disposed on the working electrode wherein the reagent matrix contains urease.

5 Claims, 9 Drawing Sheets

(56) References Cited

U.S. PATENT DOCUMENTS

| | | | |
|---|---|---|---|
| 5,846,752 | A | 12/1998 | Hausinger |
| 5,858,186 | A | 1/1999 | Glass |
| 5,945,343 | A | 8/1999 | Munkholm |
| 6,258,229 | B1 | 7/2001 | Winarta et al. |
| 6,287,451 | B1 | 9/2001 | Winarta et al. |
| 6,652,720 | B1* | 11/2003 | Mansouri et al. ......... 204/403.11 |
| 6,733,984 | B2 | 5/2004 | Delwiche et al. |
| 6,767,441 | B1 | 7/2004 | Cai et al. |
| 6,837,976 | B2 | 1/2005 | Cai et al. |
| 6,942,770 | B2 | 9/2005 | Cai et al. |
| 2001/0006149 | A1* | 7/2001 | Taniike et al. ................. 204/403 |
| 2003/0027239 | A1* | 2/2003 | Schaffar ........................... 435/25 |
| 2003/0199745 | A1* | 10/2003 | Burson et al. ................... 600/347 |
| 2004/0020777 | A1* | 2/2004 | Miyamoto et al. ............... 205/54 |
| 2004/0040866 | A1* | 3/2004 | Miyashita et al. .......... 205/777.5 |
| 2004/0245121 | A1* | 12/2004 | Nagakawa et al. ......... 205/777.5 |
| 2004/0256227 | A1* | 12/2004 | Shin et al. ................. 204/403.03 |

OTHER PUBLICATIONS

Schaffar, "Thick film biosensor for metabolites in undiluted whole blood and plasma samples," Anal. Bioanal. Chem., 2002, 254-60, 372.

Vostiar et al., "Amperometric urea biosensor based on urease and electropolymerized toluidine blue dye as a pH-sensitive redox probe," Bioelectrochemistry, 2002, 113-5, 56.

Zhang et al., "Mixed urease/amphiphile LB films and their application for biosensor development," Bioelectrochemistry, 2002, 157-8, 56.

Kovacs et al., "Optical biosensor for urea with improved response time," Biosens. & Bioelectron., 2003, 111-8, 18.

Hill et al., "Sensitivity, specificity, and predictive values of reagent test strip estimations of blood urea nitrogen," Vet. Clin. Pathol., 73-75, 23-3.

Soldatkin et al., "A novel urea sensitive biosensor with extended dynamic range based on recombinant urease and ISFETs," Biosens. & Bioelectron., 2003, 131-5, 19.

Luo et al., "Urea biosensor based on PANi(urease)-Nafion/Au composite electrode," Biosens. & Bioelectron. 2004, 15-23, 20.

Lakard et al., "Urea potentiometric biosensor based on modified electrodes with urease immobilized on polyethylenimine films," Biosens & Bioelectron., 2004, 1641-7, 19.

Reddy et al., "Immobilization of pigeonpea (*Cajanus cajan*) urease on DEAE-cellulose paper strips for urea estimation," Biotechnol. Appl. Biochem, 2004, 323-7, 39.

Yasuda et al., "Determination of urea in whole blood using a urea electrode with an immobilised urease membrane," Analyst, 1984, 61-4, 109.

Kirstein et al., "Enzyme electrode for urea with amperometric indication: Part 1—Basic principle," Biosensors, 1985, 117-30, 1.

Campanella et al., "Suitable potentiometric enzyme sensors for urea and creatinine," Analyst, 1990, 827-30, 115.

Li et al., "Application and Preparation of a BUN Test Strip," PUMC Hospital, Beijing.

Poyard et al., "Performance of urea-sensitive enzyme field effect transistors: influence of the storage conditions," C R Acad. Sci., 1996, 257-62, 319.

Della Ciana et al., "Robust, reliable biosensor for continuous monitoring of urea during dialysis," Clin. Chem,. 1996, 1079-85, 42-7.

Mizutani et al., "Voltammetric enzyme sensor for urea using mercaptohydroquinone-modified gold electrode as the base transducer," Biosens. & Bioelectron., 1997, 321-8, 12.

Jurkiewicz et al., "Development of a biparametric bioanalyser for creatinine and urea . . . " Analyst, 1998, 1321-7, 123.

Calzavara et al., "A new biosensor for continuous monitoring of the spent dialysate urea level in standard hemodialysis," Int. J. Artif. Organs, 1998, 147-50, 21-3.

Eggenstein et al., "A disposable biosensor for urea determination in blood based on an ammonium-sensitive transducer," Biosens. & Bioelectron, 1999, 33-41, 14.

Koncki et al., "Urea determination using pH-enzyme electrode," J. Pharm. & Biomed. Anal., 1999, 51-7, 21.

Arrigo et al., "Continuous urea monitoring in hemodialysis: a model approach to forecase dialytic performance. Results of a multicenter study," J. Nephrol., 2001, 481-7, 14.

Soto et al., "Characterisation and optimisation of AC conductimetric biosensors," Biosens. & Bioelectron., 2001, 23-9, 16.

Shul'gas et al., "Thin-film conductometric biosensors for glucose and urea determination," Biosens. & Bioelectron., 1994, 217-23, 9.

* cited by examiner

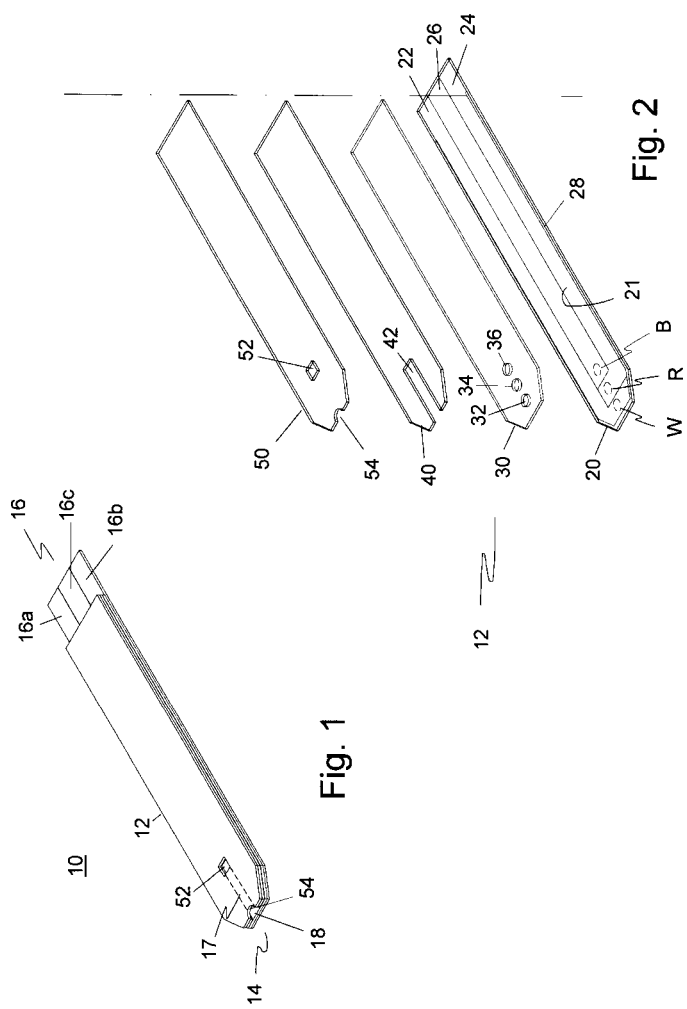

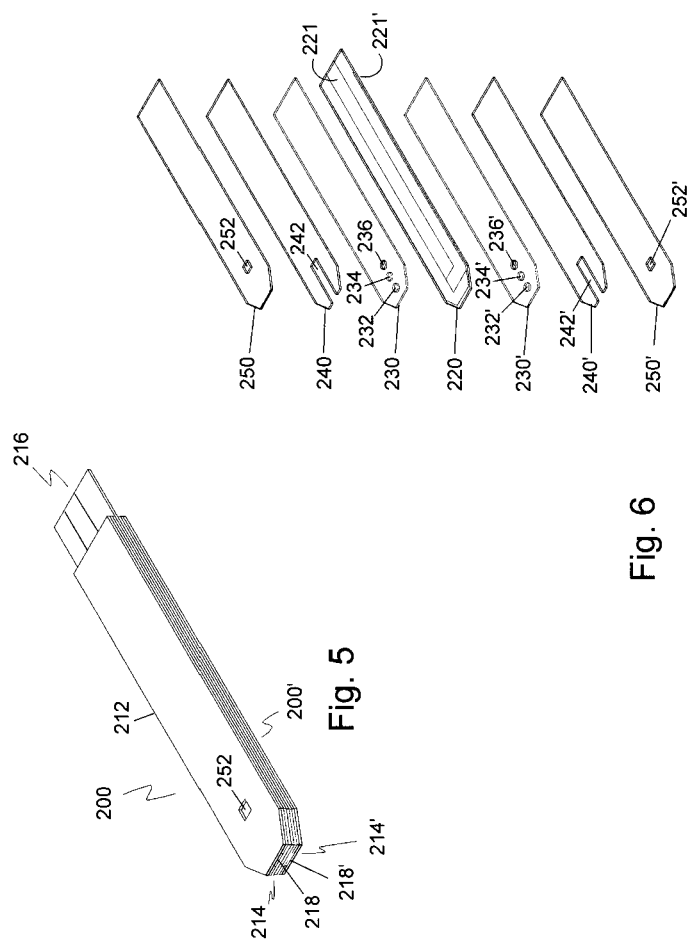

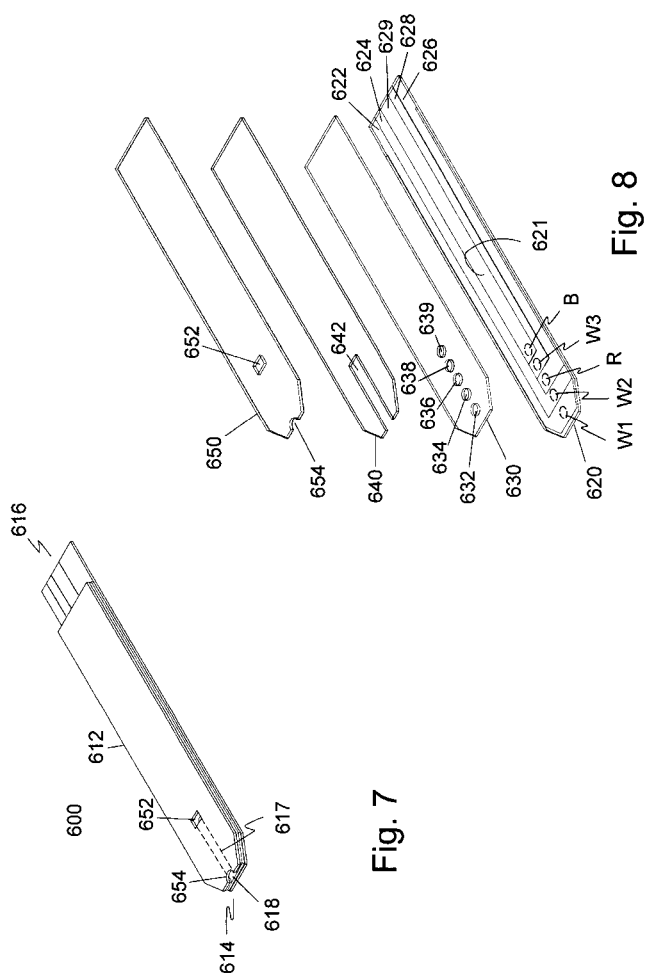

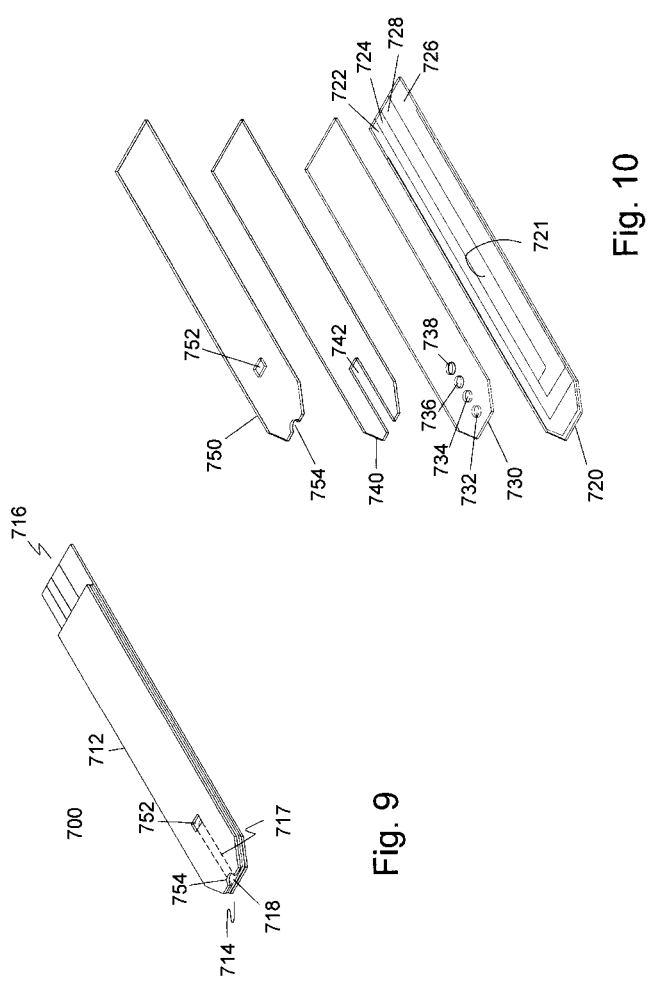

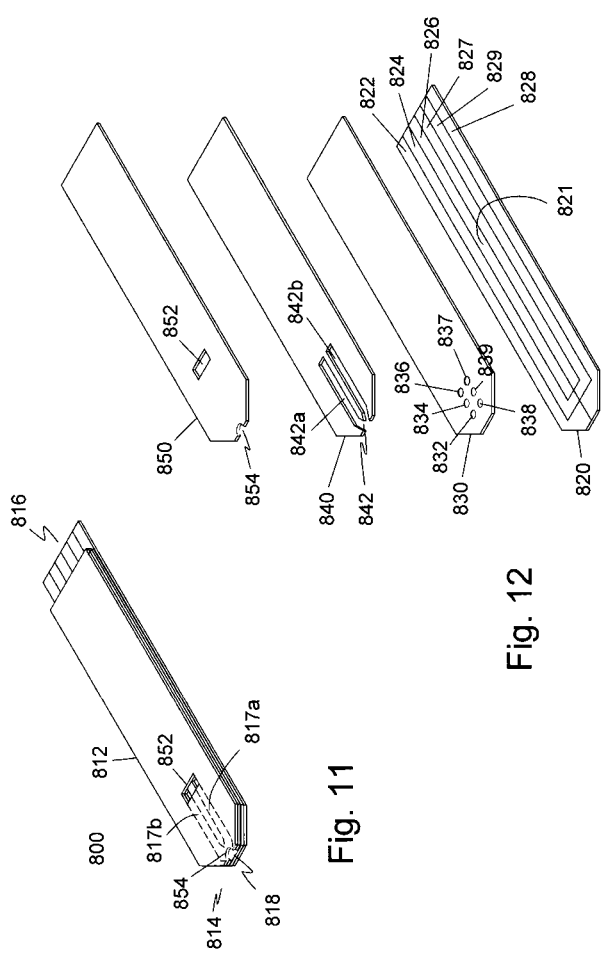

DISPOSABLE UREA SENSOR AND SYSTEM FOR DETERMINING CREATININE AND UREA NITROGEN-TO-CREATININE RATIO IN A SINGLE DEVICE

BACKGROUND OF THE INVENTION

1. Field of the Invention

The present invention relates generally to electrochemical sensors that can be used for the quantification of a specific component or analyte in a liquid sample. Particularly, the present invention relates to a disposable electrochemical sensor for measuring urea (or BUN, Blood Urea Nitrogen) in biological fluids such as blood. More particularly, the present invention relates to a system for simultaneously determining creatinine and BUN-to-creatinine ratio in a single device. Still more particularly, the present invention relates to a device that can be employed to perform assays of urea, creatinine and blood urea nitrogen-to-creatinine ratio in a small volume liquid sample (around 1 μL).

2. Description of the Prior Art

In the liver, urea is synthesized from ammonia produced as a result of de-amination of amino acids. This biosynthetic pathway is the main means of disposal of excess nitrogen by the body. Therefore, the measurement of blood urea nitrogen (BUN) is one of the most commonly used screening tests for the evaluation of kidney function. High urea concentration in blood is toxic to the body. Malfunctioning kidneys will have difficulty in getting rid of the excess urea.

There are currently several hundred thousand people with endstage renal disease in the United States. These people require regular hemodialysis. Urea is generally accepted to be the best marker for evaluating the level of uremic toxins. Hemodialysis is a procedure that has been used as a means for reduction of urea in blood. Currently, most dialysis clinics use the simple index of time of dialysis to determine the adequacy of dialysis. Drawing blood to accurately measure the level of urea in the blood is done infrequently. During this procedure, blood is drawn and sent to a central laboratory for the measurement of urea. Turnaround times for these samples can be quite long.

It has long been desired to have a sensor which could monitor the progress of the dialysis procedure in "real-time", thereby assuring that the procedure was complete and obviating the need for using clinical laboratories. A further enhancement of this general principle is a home monitor, which would allow at-home testing to monitor the peritoneal dialysis and home hemodialysis. Such a home monitor is similar, in principle, to devices used for blood glucose testing by diabetics. This device would require a blood droplet sample by using a finger prick.

There has been substantial efforts in the prior art to provide a sensor which would satisfy the above-mentioned needs, and various electrochemical sensors for detecting urea in body fluids have been proposed. These prior art devices included the use of potentiometric devices, specifically, the common pH, ammonium, or ammonia gas sensing electrodes. They also included a biosensor for urea by depositing a coating containing the enzyme urease immobilized over the interdigitated conductive members.

Other publications teach of the need for dialysis or blood urea monitoring, and various mechanical systems which could be used in such a system, albeit with different or unspecified urea detection (sensor) methods than those of the present invention. The prior approaches also describe various methods of enzyme (urease) immobilization to various substrates for detection of urea in blood or in dialysate fluid. For example, Cozzette et. al. (U.S. Pat. Nos. 5,466,575; 5,063,081) described a microfabricated BUN sensor, which is based on the potentiometric measurement of ammonium ions resulting from an enzymatic reaction. None of the previous approaches, however, describes a combination of disposable, small volume, mass fabricated sensors with dissolvable reagent matrix containing the enzyme urease.

The prior known sensors have not enabled the desired point-of-care blood test for blood urea, thereby assuring that the procedure was complete. In the absence of a reliable point-of-care blood test for blood urea, to determine whether the dialysis process is long enough to rid the excess urea, it will be desirable to have a sensor which can be used to monitor the progress of the treatment simply by measuring the blood urea concentration from a drop of blood obtained from a finger prick.

It is also well known that creatinine is a waste product derived from creatine and excreted by the kidneys. The analytical determination of creatinine in biological samples is a widely used and extremely important test for renal dysfunction. Measurements of creatinine in whole blood, serum or urine may also be used as indices in the diagnosis and treatment of other disorders such as muscular dystrophy and hypothyroidism. Thus, the creatinine assay has been widely recognized as having vital medical significance. Further, dietary changes have little, if any, influence on the creatinine concentration in blood and urine.

The BUN-to-creatinine ratio is an important index used by health professionals to predict what conditions may be causing abnormal BUN and creatinine levels and decreased kidney function. The normal values for the BUN-to-creatinine ratio are typically in the 10:1 to 20:1 range for persons over 12 months of age and up to 30:1 for infants less than 12 months of age. A high BUN value can indicate kidney injury or diseases, such as, diabetes, high blood pressure, kidney stone, or tumor. It can also be caused by reduced blood flow to the kidneys caused by dehydration or heart failure. Certain medications may also cause high BUN values.

High BUN-to-creatinine ratios occur with sudden kidney failure, which may be caused by conditions such as shock or severe dehydration. An obstruction in the urinary tract can also cause an elevated BUN-to-creatinine ratio. A very high BUN-to-creatinine ratio may be caused by bleeding in the digestive tract or respiratory tract.

On the other hand, a low BUN value may be caused by a diet very low in protein, malnutrition, or severe liver damage. Drinking excessive amounts of liquid may cause overhydration and lead to a low BUN value.

Low BUN-to-creatinine ratios may be associated with a diet low in protein, severe muscle injury called rhabdomyolysis, pregnancy, cirrhosis, or syndrome of inappropriate antidiuretic hormone secretion (SIADH). SIADH sometimes occurs with lung disease, cancer, diseases of the central nervous system, and the use of certain medications.

Therefore, what is needed is a disposable sensor capable of measuring urea in a small volume of body fluid sample such as blood. What is also needed is a disposable sensor capable of measuring urea in a small volume of body fluid such as blood obtained by lancing the skin of a user. What is further needed is a system for determining the blood urea, creatinine and blood urea nitrogen-to-creatinine ratio in a small volume of body fluid using a single device.

SUMMARY OF THE INVENTION

It is an object of the present invention to provide a disposable urea sensor capable of measuring the urea concentration in a small volume of body fluid. It is another object of the present invention to provide a disposable urea sensor that is capable of measuring the urea concentration in a small volume of body fluid such as blood obtained by lancing the skin of the user. It is a further object of the present invention to provide a disposable urea sensor that has a fast response time. It is yet another object of the present invention to provide a disposable sensor for use in determining urea, creatinine and BUN-to-creatinine ratio in a body fluid sample. It is still another object of the present invention to provide a system for determining urea, creatinine and BUN-to-creatinine ratio in a blood sample with a single disposable device.

The present invention provides these and other objectives in the following described embodiments.

In the first embodiment of the present invention, the sensor of the present invention uses a 4-layer laminated construction, similar to the glucose sensor, which has been disclosed in the following U.S. Pat. Nos. 6,767,441; 6,287,451; 6,837,976, which are incorporated herein by reference.

In one aspect of the first embodiment, the sensor of the present invention has a laminated, elongated body having a sample fluid channel connected between an opening on one end of the laminated body and a vent hole spaced from the opening. Within the fluid channel lie at least one working electrode and a reference electrode (or a counter electrode). The arrangement of the at least one working electrode and the reference electrode (or the counter electrode) is not important for purposes of the results obtained from the sensor. The at least one working electrode and the reference electrode are each in electrical contact with separate conductive paths. The separate conductive paths terminate and are exposed for making an electrical connection to a reading device on the end opposite the open channel end of the laminated body.

In another aspect of the first embodiment, the laminated body has a base insulating layer made from a plastic material. At least two conductive paths are delineated on the base insulating layer. The conductive paths may be deposited on the insulating layer by screen printing, by vapor deposition, or by any method that provides for a conductive layer that adheres to the base insulating layer. The conductive paths can be individually disposed on the insulating layer, or a conductive layer may be disposed on the insulating layer followed by etching/scribing the required number of conductive paths. The etching process may be accomplished by chemically, mechanically scribing lines in the conductive layer, using a laser to scribe the conductive layer into separate conductive paths, or by any means that will cause a break between and among the separate conductive paths required by the present invention. Conductive coatings or layers that may be used are coatings of nickel, gold, tin oxide/gold, palladium, other noble metals or their oxides, or carbon film compositions. The preferred conductive coatings are gold film or a tin oxide/gold film composition.

In a further aspect of the first embodiment of the present invention, the laminated body has a first middle insulating layer, also called a reagent holding/electrode area defining layer, on top of the base insulating layer and the conductive paths. The first middle layer, or reagent holding layer, contains at least two opening for one or more working electrodes and one or more reference electrodes. Each opening corresponds to and exposes a small portion of an electrode surface. The openings for the one or more working electrodes may be the same or different size, but preferably the same size. The opening for the one or more reference electrodes may be the same or different size as the openings for the one or more working electrodes, but preferably the same size. The placement of all of the openings is such that they will be all positioned within the sample fluid channel described above. The first middle insulating layer is also made of an insulating dielectric material, preferably plastic, and may be made by die cutting the material mechanically, or with a laser, and then fastening the material to the base layer. An adhesive, such as a pressure-sensitive adhesive, may be used to secure the first middle insulating layer to the base layer. Adhesion may also be accomplished by ultrasonically bonding the first middle layer to the base layer. The first middle insulating layer may also be made by screen printing an insulating material or by binding a photopolymer over the base layer.

In yet another aspect of the first embodiment, the laminated body also has a second middle insulating layer, called a channel-forming layer, on top of the first middle layer. The second middle layer, or channel-forming layer, is also made of a plastic insulating material and creates the sample fluid channel of the laminated body. It contains a U-shaped cutout on one end which overlays the openings on the first middle layer with the open end corresponding to the open end of the laminated body described earlier. A double coated, pressure-sensitive adhesive tape may be used as the second middle layer.

In yet another aspect of the first embodiment, the laminated body of the present invention has a top layer with a vent opening and preferably an entrance notch. The vent opening is located such that at least a portion of the vent opening overlays the bottom of the U-shaped cutout of the second middle insulating layer. The vent allows air within the sample fluid channel to escape as the sample fluid enters the sample entrance end of the laminated body. The notch is located at the sample entrance end. The sample fluid generally fills the sample fluid channel by capillary action. In small volume situations, the extent of capillary action is dependent on the hydrophobic/hydrophilic nature of the surfaces in contact with the fluid undergoing capillary action. Capillary forces are enhanced by either using a hydrophilic insulating material to form the top layer, or by coating at least a portion of one side of a hydrophobic insulating material with a hydrophilic substance in the area of the top layer that faces the sample fluid channel between the sample entrance end of the laminated body and the vent opening of the top layer. It should be understood that an entire side of the top layer may be coated with the hydrophilic substance and then bonded to the second middle layer.

In yet another aspect of the first embodiment, one opening contains electrode material for the working electrode (W) loaded with urea sensitive enzyme (urease) and other ingredients, and one opening for the reference electrode (R). The positional arrangement of the working electrode and the reference electrode in the channel is not critical for obtaining usable results from the electrochemical sensor. The possible electrode arrangements within the sample fluid channel may be W-R or R-W, with the arrangement listed as the arrangement of electrodes would appear from the sample entrance end of the laminated body to the vent opening. The preferred position was found to be W-R; that is, as the sample fluid entered the entrance open end of the laminated body, the fluid would cover W first, then R. The preferred position obviates reliability and accuracy problems due to an insufficient sample fluid size. The working electrode and the reference electrode are each in electric contact with separate conductive paths, respectively. The separate conductive paths terminate and are exposed for making an electric connection to a reading device on the end opposite the sample entrance end of the laminated body.

In a further aspect of the first embodiment, the working electrode is loaded with a mixture of at least an enzyme (urease), and optionally with one or more of a surfactant, a polymer binder, and a buffer. The reference electrode may be loaded with the same mixture as the working electrode, with an addition of a redox mediator (oxidized form), or a mixture of both reduced and oxidized form of redox mediators. Preferably, the reference electrode opening is loaded with an oxidized form of redox mediator, such as potassium ferricyanide, along with other ingredients. The reference electrode opening could also be loaded with an Ag/AgCl layer (e.g., by applying Ag/AgCl ink or by sputter-coating silver or an Ag/AgCl layer) or other reference electrode materials.

In a yet further aspect of the first embodiment, when a liquid sample is applied to the sensor of the present invention, the sample fills up the entire channel and covers both working electrode and reference electrode (or counter electrode). When a positive potential (e.g. 0.4 V vs. the reference electrode; if the reference electrode opening is loaded with a redox mediator in oxidized form, such as potassium ferricyanide) is imposed across the working and reference electrodes, surprisingly, an oxidation current signal, related to the urea concentration in the sample, is observed. The current response is proportional to the urea concentration over the entire concentration range of clinical importance. The detail mechanism for the involved enzymatic and electrochemical reactions and the urea signal are not clear. It has been found that the urease loading for the working electrode is essential for the generation of the electrochemical signal of urea in the sample. In most enzyme-based electrochemical sensors, e.g. glucose strips, a redox mediator or oxygen is always involved at the working electrode in order to generate the useful electrochemical signal. In contrast to the conventional enzyme-based electrochemical sensors, the redox mediators at the working electrode of the BUN sensor of the present invention are not required to obtain the electrochemical response of urea.

In the second embodiment of the present invention, the sensor of the present invention has a similar structure to the first embodiment, but it has one working electrode, one reference electrode and one blank electrode. The working electrode is loaded with a urea sensitive enzyme (urease) and other ingredients; the blank electrode is loaded with a similar chemistry except without adding a urea sensitive enzyme. Such a three-electrode system not only possesses the feature of the first embodiment, but also the capability of eliminating interference from any oxidizable species in the sample, such as ascorbic acid, acetaminophen, uric acid, etc.

In one aspect of the second embodiment, at least three conductive paths are delineated on the base insulating layer. The first middle layer, or reagent holding layer, contains at least three openings for one working electrode, a reference electrode and one blank electrode.

In another aspect of the second embodiment, one opening contains electrode material for the working electrode (W) loaded with urease and other ingredients; one for the blank electrode (B) loaded with similar chemistry to W, without adding urease; and one for the reference electrode (R). The positional arrangement of the working electrode, the reference electrode and the blank electrode in the channel is not critical for obtaining usable results from the electrochemical sensor. The preferred position was found to be W1-R-B; that is, as the sample fluid entered the entrance open end of the laminated body, the fluid would cover W first, then R, then B.

In the third embodiment of the present invention, the sensor of the present invention has a similar structure to the first embodiment, but without the first middle layer; i.e., the other three layers are the same as in the first embodiment. The detail of such a 3-layer layout has been disclosed in U.S. Pat. Nos. 6,258,229; 6,942,770, which are incorporated herein by reference. The U-shaped channel cutout is located at the sensor end (sample entrance end). The length, thickness and width of the U-shaped channel cutout define the capillary channel size or volume. The length and width of the U-shaped channel cutout, along with the base conductive layer, define the areas of the working and reference electrodes.

In one aspect of the third embodiment, the working electrode (W) is loaded with at least a urea sensitive enzyme (urease), and optionally with one or more of a polymer binder, one or more of a surfactant and one or more of a buffer. The reference electrode (R) is preferably covered by the same reagent mixture as the working electrode with an addition of at least a redox mediator. Instead of the reagent mixture, the reference electrode could also be covered with an Ag/AgCl layer (e.g., by applying Ag/AgCl ink or by sputter-coating silver or an Ag/AgCl layer) or other reference electrode materials.

In the fourth embodiment of the present invention, the sensor of the present invention has a similar structure to the first embodiment, but it has two additional working electrodes: one loaded with creatinine/creatine sensitive enzymes and other ingredients; the other loaded with creatine sensitive enzymes and other ingredients. Such a four-electrode system, arranged in one channel, not only possesses the feature of the first embodiment, but also the capability of measuring creatinine and creatine in the sample. Thus, the urea nitrogen-to-creatinine ratio can be calculated. Details of the creatinine/creatine sensor have been disclosed in U.S. Pat. No. 6,767,441.

In one aspect of the fourth embodiment, at least four conductive paths are delineated on the base insulating layer. The first middle layer, or reagent holding layer, contains at least four openings for three working electrodes and a reference electrode.

In another aspect of the fourth embodiment, one opening contains electrode material for the first working electrode (W1) loaded with urease and other ingredients, one for the second working electrode (W2) loaded with creatinine/creatine sensitive enzymes and other ingredients, one for the third working electrode (W3) loaded with creatine sensitive enzymes and other ingredients, and one for the reference electrode (R). The positional arrangement of the working electrodes and the reference electrode in the channel is not critical for obtaining usable results from the electrochemical sensor. The preferred position was found to be W1-W2-R-W3; that is, as the sample fluid entered the open end of the laminated body, the fluid would cover W1 first, then W2, then R, then W3.

In still another aspect of the fourth embodiment, in order for the reference electrode to function properly for all of the three working electrodes, the reference electrode opening may be loaded with at least a polymer, a surfactant, a buffer, with an addition of at least a redox mediator (either reduced form, e.g. potassium ferrocyanide, or oxidized form, e.g. potassium ferricyanide) or a mixture of a reduced form redox mediator and an oxidized form redox mediator. Preferably, a mixture of a reduced form redox mediator and an oxidized form redox mediator is loaded onto the reference electrode opening. Instead of the reference reagent mixture disclosed above, the reference electrode opening could also be loaded with an Ag/AgCl layer (e.g., by applying Ag/AgCl ink or by sputter-coating a silver or Ag/AgCl layer) or other reference electrode materials.

In the fifth embodiment of the present invention, the sensor of the present invention has a similar structure to the second embodiment, but it has two additional working electrodes, i.e., in the one single channel, there are at least four working electrodes and one reference electrode.

In one aspect of the fifth embodiment, at least five conductive paths are delineated on the base insulating layer. The first middle layer, or reagent holding layer, contains at least five openings for the five working electrodes and one reference electrode.

In another aspect of the fifth embodiment, the first working electrode (W1) is loaded with a urea sensitive enzyme (urease) and other ingredients; the second working electrode (W2) is loaded with creatinine/creatine sensitive enzymes and other ingredients; the third working electrode (W3) is loaded with creatine sensitive enzymes and other ingredients; the blank electrode (B) is preferably loaded with the same chemistry as W1 without adding any enzyme. Such a five-electrode system (including the reference electrode), in a single device, not only possesses the feature of the second embodiment, having the capability of eliminating interference from any oxidizable species in the sample, but also possesses the capability of measurement of creatinine and blood urea nitrogen-to-creatinine ratio.

In still another aspect of the fifth embodiment, in order for the reference electrode to function properly for all of the four working electrodes, the reference electrode opening may be loaded with at least a polymer, a surfactant, a buffer, with an addition of at least a redox mediator (either reduced form, e.g. potassium ferrocyanide, or oxidized form, e.g. potassium ferricyanide) or a mixture of a reduced form redox mediator and an oxidized form redox mediator. Preferably, a mixture of a reduced form redox mediator and an oxidized form redox mediator is loaded onto the reference electrode opening. Instead of the reference reagent mixture disclosed above, the reference electrode opening could also be loaded with an Ag/AgCl layer (e.g., by applying Ag/AgCl ink or by sputter-coating a silver or Ag/AgCl layer) or other reference electrode materials.

In still another aspect of the fifth embodiment, the positional arrangement of the working electrodes, the blank electrode and the reference electrode in the channel is not critical for obtaining usable results from the electrochemical sensor. There are numerous combinations for the positional arrangement. For example, one possible arrangement is W1-B-R-W2-W3; that is, as the sample fluid enters the entrance open end of the laminated body, the fluid would cover W1 first, then B, then R, then W2, then W3.

In the sixth embodiment of the present invention, the sensor of the present invention has a similar structure to the fifth embodiment, but at least five conductive paths are delineated on the base insulating layer: one for the BUN working electrode (W1); one for the creatinine/creatine working electrodes (W2); one for creatine working electrode (W3); one for the BUN reference electrode (R1) and one for the creatinine/creatine reference electrode (R2). Accordingly, the first middle layer, or reagent holding layer, contains at least five openings for three working electrodes and two reference electrodes.

In one aspect of the sixth embodiment, one opening contains electrode material for the first working electrode (W1) loaded with urease and other ingredients; one for the second working electrode (W2) loaded with creatinine/creatine sensitive enzymes and other ingredients; one for the third working electrode (W3) loaded with creatine sensitive enzymes and other ingredients; one for the BUN reference electrode (R1) and one for the combined creatinine/creatine and creatine reference electrode (R2). The positional arrangement of the working electrodes and the reference electrodes in the channel is not critical for obtaining usable results from the electrochemical sensor. There are numerous combinations for the positional arrangement. For example, one possible arrangement is W3-W2-R2-R1-W1; that is, as the sample fluid enters the entrance open end of the laminated body, the fluid would cover W3 first, then W2, then R2, then R1, then W1.

In another aspect of the sixth embodiment, the BUN sensor (W1) and creatinine/creatine sensors (W2/W3) have separate reference electrodes. The reference electrode for W1 will be similar to those described in the first embodiment; the reference electrode for W2/W3 is preferably loaded with a reduced form of redox mediator, such as potassium ferrocyanide, and other ingredients as disclosed in U.S. Pat. No. 6,767,441.

In another aspect of the sixth embodiment, creatinine/creatine reference electrodes are loaded with at least a redox mediator, a polymer binder, a surfactant, and a bulking reagent. The the redox mediators for the creatinine/creatine reference electrode are preferably in their reduced form, such as for example potassium ferrocyanide. The reference electrodes opening could also be loaded with an Ag/AgCl layer (e.g., by applying Ag/AgCl ink or by sputter-coating silver or an Ag/AgCl layer) or other reference electrode materials.

In still another aspect of the sixth embodiment, at least five conductive paths are delineated on the base insulating layer: one for the BUN working electrode; two for the creatinine/creatine working electrodes; one for the BUN reference electrode and one for the creatinine/creatine reference electrode. The first middle layer, or reagent holding layer, contains at least five openings for three working electrodes and two reference electrodes.

In still another aspect of the sixth embodiment, at least four conductive paths are delineated on the base insulating layer: one for the BUN working electrode; two for the creatinine/creatine working electrodes; one for the combined BUN and creatinine/creatine reference electrode, although there are two reference electrode openings which may be loaded with different chemical reagents. The first middle layer, or reagent holding layer, contains at least five openings for three working electrodes and two reference electrodes. The BUN reference electrode opening is preferably loaded with an oxidized form of redox mediator, such as potassium ferricyanide and other ingredients; the creatinine/creatine reference electrode opening is preferably loaded with a reduced form of redox mediator, such as potassium ferrocyanide, and other ingredients. Note that there are two reference electrode openings and they may be loaded with different chemical reagents.

In the seventh embodiment of the present invention, the sensor of the present invention has a similar structure to the fifth embodiment, but at least six conductive paths are delineated on the base insulating layer: one for the BUN working electrode (W1); one for the BUN blank electrode (B); one for the creatinine/creatine working electrodes (W2); one for creatine working electrode (W3); one for the combined BUN reference electrode (R1) and one for the creatinine/creatine reference electrode (R2). Accordingly, the first middle layer, or reagent holding layer, contains at least six openings for three working electrodes, one blank electrode and two reference electrodes.

In one aspect of the seventh embodiment, one opening contains electrode material for the first working electrode (W1) loaded with urease and other ingredients; one for the blank electrode (B); one for the second working electrode (W2) loaded with creatinine/creatine sensitive enzymes and other ingredients; one for the third working electrode (W3) loaded with creatine sensitive enzymes and other ingredients; one for the BUN reference electrode (R1) and one for the creatinine/creatine reference electrode (R2).

In the eighth embodiment of the present invention, the sensor of the present invention has two channels (Channel 1 and Channel 2) on the same strip, arranged side by side. At least one channel serves as the urea sensor having a similar structure to those mentioned in the above embodiments; at least one channel serves as the creatinine sensor. The sample entrance ends, or sampling entrances of the two channels, are close to each other; or the two channels simply share the same sampling entrance. In either case, the two channels are able to use the same drop of the blood sample.

In one aspect of the eighth embodiment, the number of the base conductive paths on the base insulating layer should match the total number of the electrodes in Channel 1 and Channel 2. There are two rows of openings on the second middle layer, one used for Channel 1 and the other one for Channel 2. Accordingly, the second middle layer has two U-shape cutouts, one used for the Channel 1 and the other one for Channel 2. The laminated body also has a top layer with a vent opening for each channel. The two channels can also share one larger vent opening. Preferably each has an entrance notch at the sample entrance end. More preferably, the two channels share the same entrance notch, so that two channels are able to use the same drop of the blood sample.

In another aspect of the eighth embodiment, Channel 1 has at least one working electrode and one reference electrode. At least one of the working electrodes is loaded with urease and other ingredients. Channel 1 can function independently as a urea sensor.

In still another aspect of the eighth embodiment, Channel 2 has at least two working electrodes and one reference electrode. One of the working electrodes is loaded with creatinine/creatine sensitive enzymes and other ingredients and the other one is loaded with creatine sensitive enzymes. Channel 2 can function independently as a creatinine sensor. However, if creatine interference is not a concern, Channel 2 may incorporate only one working electrode for the creatinine/creatine sensitive enzymes.

In a ninth embodiment of the present invention, the sensor of the present invention has two channels (Channel 1 and Channel 2) on the same strip, arranged back to back (or top/bottom arrangement). At least one channel (e.g. Channel 1) serves as the urea sensor having a similar structure to those mentioned in the above embodiments; at least one channel (e.g. Channel 2) serves as the creatinine sensor. The sample entrance ends, or sampling entrances of the two channels, are close to each other; or the two channels simply share the same sampling entrance, such that the two channels are able to use the same drop of the blood sample. Either channel can be arranged on the top (or bottom).

In one aspect of the ninth embodiment, there are total of nine laminated layers. The first four layers are used for the Channel 1; last four layers for the Channel 2; while the fifth layer, located in the middle of the nine laminated layers, is a layer of adhesive, glue or double-sided tape, binding the two channels together in a back-to-back configuration.

In another aspect of the ninth embodiment, there are total of seven laminated layers. The two channels share the same base insulating layer. This base layer has conductive paths on both sides; one side used for Channel 1 and the other one for Channel 2.

In still another aspect of the ninth embodiment, Channel 1 has at least one working electrode and one reference electrode. At least one of the working electrodes is loaded with urease and other ingredients. Channel 1 can function independently as a urea sensor.

In further aspect of the ninth embodiment, Channel 2 has at least two working electrodes and one reference electrode. One of the working electrodes is loaded with creatinine/creatine sensitive enzymes and other ingredients and the other one is loaded with creatine sensitive enzymes. Channel 2 can function independently as a creatinine sensor.

In yet another embodiment of the present invention, the disposable strip has a sensor body with an open well forming a test chamber, a working electrode and a reference electrode within the test chamber, and electrical contacts for electrically connecting the working electrode and the reference electrode to a meter device. The test chamber contains a reagent on at least the working electrode where the reagent contains at least urease. The meter device must be capable of providing a biasing potential across the working electrode and the reference electrode and detecting a current generated by the presence of urea in a fluid sample disposed into the open well of the disposable strip.

The above described embodiments are based on amperometric analyses. Those skilled in the art, however, will recognize that a sensor of the invention may also utilize coulometric, potentiometric, voltammetric, and other electrochemical techniques to determine the concentration of an analyte in a sample.

All of the advantages of the present invention will be made clearer upon review of the detailed description, drawings and appended claims.

BRIEF DESCRIPTION OF THE DRAWINGS

FIG. 1 is a perspective view of one embodiment of the present invention showing the test strip.

FIG. 2 is an exploded view of the embodiment in FIG. 1 showing the four component layers of the test strip.

FIG. 5 is a perspective view of another embodiment of the present invention showing the combination of a BUN sensor strip and a creatinine sensor strip where the base layer is common to both sensors.

FIG. 6 is an exploded view of the embodiment in FIG. 5 showing the arrangement of the component layers of the BUN sensor and the creatinine sensor.

FIG. 7 is a perspective view of another embodiment of the present invention showing a combined sensor strip having four working electrodes, namely a BUN measuring electrode, a blank working electrode, a creatinine measuring electrode, a creatine working electrode, and a reference electrode.

FIG. 8 is an exploded view of the embodiment in FIG. 7 showing the arrangement of the component layers.

FIG. 9 is a perspective view of another embodiment of the present invention showing a combined sensor strip having three working electrodes namely, a BUN measuring electrode, a creatinine measuring electrode and an interferent-compensating electrode.

FIG. 10 is an exploded view of the embodiment in FIG. 9 showing the arrangement of the component layers that includes the BUN measuring electrode, creatinine measuring electrode, the interferent-compensating electrode, and a reference electrode.

FIG. 11 is a perspective view of another embodiment of the present invention showing a combined sensor strip having a BUN sensor system side-by-side with the creatinine sensor system.

FIG. 12 is an exploded view of the embodiment in FIG. 9 showing the arrangement of the component layers that includes the BUN sensor system and the creatinine sensor system.

DETAILED DESCRIPTION OF THE PREFERRED EMBODIMENT

Figure 4:
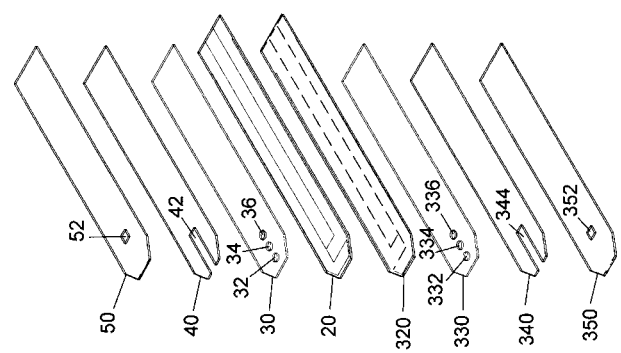
FIG. 4 is an exploded view of the embodiment in FIG. 3 showing the arrangement of the component layers of the BUN sensor strip and the creatinine sensor strip.

The preferred embodiment(s) of the present invention is illustrated in FIGS. 1-15. FIG. 1 shows a urea sensor 10 of the present invention. Sensor 10 has a laminated body 12, a fluid sampling end 14, an electrical contact end 16, and a vent opening 52. Sensor 10 may also include an optional inlet notch 54. Fluid sampling end 14 includes a sample chamber 17 between a sampling end inlet 18 and vent opening 52. Electrical contact end 16 has three discrete conductive contacts 16a, 16b and 16c.

Referring now to FIG. 2, laminated body 12 is composed of a base layer 20, a reagent holding layer 30, a channel forming layer 40, and a cover 50. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

Base layer 20 has a conductive layer 21 on which is delineated three conductive paths 22, 24 and 26. The conductive paths 22, 24 and 26 may be formed by scribing or scoring conductive layer 21, or by silk-screening conductive paths 22, 24 and 26 onto base layer 20. Scribing or scoring of conductive layer 21 may be done by mechanically scribing the conductive layer 21 sufficiently to create at least three independent conductive paths 22, 24 and 26. The preferred scribing or scoring method of the present invention is done by using a carbon dioxide laser, a YAG laser or an eximer laser. An additional scoring line 28 (enlarged and not to scale; for illustrative purposes only) may be made, but is not necessary to the functionality of sensor 10, along the outer edge of base layer 20 in order to avoid potential static problems which could give rise to a noisy signal. Conductive layer 21 may be made of any electrically conductive material such as, for example, gold, tin oxide/gold, palladium, other noble metals or their oxides, or carbon film compositions. The preferred electrically conductive material is gold or tin oxide/gold. A usable material for bottom layer 20 is a tin oxide/gold polyester film (Cat. No. FM-1) or a gold polyester film (Cat. No. FM-2) sold by Courtaulds Performance Films, Canoga Park, Calif.

Reagent holding layer 30 has a first electrode opening 32 which exposes a portion of first conductive path 22, a second electrode opening 34 which exposes a portion of second conductive path 24, and a third electrode opening 36 which exposes a portion of third conductive path 26. Reagent holding layer 30 is made of a plastic material, preferably a medical grade, one-sided adhesive tape available from Adhesive Research, Inc., of Glen Rock, Pa. Acceptable thicknesses of the tape for use in the present invention are in the range of about 0.001 in. (0.025 mm) to about 0.01 in. (0.25 mm). One such tape, Arcare® 7815 (about 0.003 in. (0.075 mm)), is preferred due to its ease of handling and its ability to promote capillary action through the sample chamber of the sensor. It should be understood that the use of a tape is not required. Reagent holding layer 30 may be made from a plastic sheet and may be coated with a pressure sensitive adhesive, a photopolymer, ultrasonically-bonded to base layer 20, or silk-screened onto the base layer 20 to achieve the same results as using the polyester tape mentioned.

The three electrode openings 32, 34 and 36 define electrode wells W, R and B, respectively, and hold chemical reagents forming a working electrode, a reference electrode, and a blank electrode. Generally, electrode well W is loaded with a BUN reagent matrix that contains the urea sensitive enzyme, urease, but no redox mediator and preferably at least a polymer binder, a surfactant and a buffer. Electrode well B is loaded with a similar chemistry to W, without adding the urea sensitive enzyme, urease, or redox mediator. One or more chemical components such as polymers, stabilizers, and bulking agents may be optionally included in the BUN reagent matrix and/or the blank reagent matrix. A reference matrix is loaded in electrode well R.

Typically, the reference matrix contains at least a redox reagent/couple or mediator such as, a reduced form of redox mediator, an oxidized form of redox mediator, or a mixture of a reduced and oxidized form of redox mediators. For example, a mixture of potassium ferricyanide and potassium ferrocyanide may be loaded to make the reference electrode function when using the preferred conductive coating material. The mixture of potassium ferricyanide and potassium ferrocyanide may be prepared such that the potassium ferricyanide concentration is in the range of about 5% to about 10%, preferably 10%, while the potassium ferrocyanide concentration is in the range of about 0% to about 5%. If R is not loaded with a redox reagent/couple or mediator, working electrode W will not function properly. In the alternative, the reference electrode (electrode well R) may be loaded with a Ag/AgCl layer (e.g., by applying Ag/AgCl ink or by sputter-coating (a) a Ag layer followed by chloridizing the Ag or (b) a Ag/AgCl layer) or other reference electrode materials that do not require a redox mediator to function properly.

The preferred shape of the reagent holding openings is round and has a preferred diameter of about 0.03 in. (0.76 mm). The three reagent holding/electrode openings 32, 34 and 36 are aligned with each other and are spaced preferably about 0.025 in. (0.64 mm) from each other. The circular reagent holding openings are for illustrative purposes only. It should be understood that the shape and size of the reagent holding openings as well as the distance between the reagent holding openings are not critical, provided that the size of the openings is big enough to facilitate dispensing chemical reagents but small enough to allow for a reasonably small sample channel.

The positional arrangement of the working electrodes and the reference electrode in the sample chamber is not critical for obtaining usable results from the BUN sensor. The possible electrode arrangements within the sample chamber may be W-B-R, W-R-B, R-W-B, B-W-R, B-R-W, or R-B-W, with the arrangement listed as the arrangement of electrodes would appear from the sample inlet 18 of laminated body 12 to the vent opening 52. The preferred position was found to be W-R-B; that is, as the fluid sample enters sampling end 14 of laminated body 12, the fluid sample would cover W first, then R followed by B. Such an arrangement may be beneficial for obtaining usable results when the sample size is insufficient or partially insufficient.

The working electrode, the blank electrode and the reference electrode are all in electric contact with separate conductive paths. The separate conductive paths terminate and are exposed for making an electrical connection to a reading device on the end opposite the sample inlet 18 of laminated body 12.

Channel forming layer 40 has a U-shaped cutout 42 located at the fluid sampling end 14. The length of cutout 42 is such that when channel forming layer 40 is laminated to reagent holding layer 30, electrode areas W, R and B are within the space defined by cutout 42. The length, width and thickness of the U-shaped cutout 42 define the capillary chamber volume. The thickness of channel forming layer 40 can affect the speed of the sample fluid flow into the sample chamber, which is filled by capillary action of the sample fluid. Channel forming layer 40 is made of a plastic material, preferably a medical grade, double-sided pressure-sensitive adhesive tape available from Adhesive Research, Inc., of Glen Rock, Pa. Acceptable thicknesses of the tape for use in the present invention are in the range of about 0.001 in. (0.025 mm) to about 0.010 in. (0.25 mm). One such tape is Arcare® 7840 (about 0.0035 in. (0.089 mm)). U-shaped cutout 42 can be made with a laser or by die-cutting. The preferred method is to die-cut the cutout. The preferred size of the U-shaped cutout is about 0.201 in. long (5.12 mm), about 0.05 in. wide (1.27 mm), and about 0.005 in. thick (0.127 mm).

Cover 50, which is laminated to channel forming layer 40, has vent opening 52 spaced from fluid sampling end 14 of BUN sensor 10 to ensure that the sample in the sample chamber 17 will completely cover electrode areas W, R and B. Vent opening 52 is positioned in cover 50 so that it will align somewhat with U-shaped cutout 42. Preferably, vent opening 52 will expose a portion of and partially overlay the bottom of the U-shaped cutout 42. The preferable shape of vent opening 52 is a rectangle with dimensions of about 0.08 in. (2 mm) by about 0.035 in. (0.9 mm). The preferred material for cover 50 is a polyester film. In order to facilitate the capillary action, it is desirable for the polyester film to have a highly hydrophilic surface that faces the capillary chamber. Transparency films (Cat. No. PP2200 or PP2500) from 3M are the preferred material used as the cover in the present invention. Cover 50 may optionally include inlet notch 54.

Figure 3:
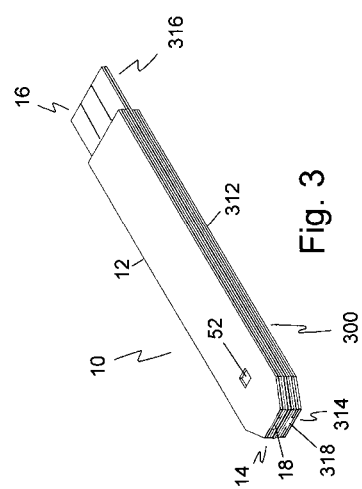
FIG. 3 is a perspective view of another embodiment of the present invention showing the combination of a BUN sensor strip and a creatinine sensor strip.

FIG. 3 shows a combination of a BUN sensor 10 and a creatinine sensor 300. Both BUN sensor 10 and creatinine sensor 300 are made of the 4-layer construction where the bottoms of each sensor are laminated to each other forming an integrated BUN/creatinine sensor combination. Each sensor has a laminated body 12, 312, a fluid sampling end 14, 314, an electrical contact end 16, 316, and a vent opening 52, 352 (not shown). Fluid sampling ends 14, 314 include sample chambers (not shown) between sampling end inlets 18, 318 and vent openings 52, 352, respectively.

Turning now to FIG. 4, each sensor 10, 300 has a base layer 20, 320, a reagent holding layer 30, 330, a chamber forming layer 40, 340, and a cover 50, 350. Reagent holding layers 30, 330 have reagent holding openings 32, 34, 36 and 332, 334, 336, respectively. Channel forming layers 40, 340 have U-shaped cutouts 42, 342, respectively. Typically, an adhesive is used to hold sensors 10 and 300 together. Preferably, an additional layer (not shown) with adhesive on both sides is used to facilitate assembly of sensor 10 to sensor 300.

FIG. 5 illustrates a BUN and a creatinine sensor combination with a 7-layer laminated body 212. The combination includes a BUN sensor 200 and a creatinine sensor 200'. Laminated body 212 includes a fluid sampling end 214, an electrical contact end 216 and vent openings 252, 252' (not shown). Fluid sampling end 214 includes two sample chambers (not shown: one between sampling end inlet 218 and vent opening 252 and the other between sampling end inlet 218' and vent opening 252' (not shown).

FIG. 6 shows an expanded view of laminated body 212 of the embodiment in FIG. 5. Laminated body 212 has a central, base layer 220 with a conductive coating 221, 221' on each side, delineating the conductive paths for the working and reference electrodes of each sensor. Each side of central, base layer 220 includes a reagent holding layer 230, 230', a channel forming layer 240, 240', and a cover 250, 250'. Reagent holding layers 230, 230' have reagent holding openings 232, 234, 236 and 232', 234', 236', respectively. Channel forming layers 240, 240' have U-shaped cutouts 242, 242', respectively.

FIG. 7 illustrates yet another embodiment of the present invention showing a combination BUN/creatinine sensor. FIG. 7 shows a combination BUN/creatinine sensor 600 with a laminated body 612, a fluid sampling end 614, an electrical contact end 616, and a vent opening 652. Sensor 600 may optionally include an inlet notch 654. Fluid sampling end 614 includes a sample chamber 617 between sample inlet 618 and vent opening 652.

FIG. 8 shows an expanded view of laminated body 612 of the embodiment in FIG. 7. Laminated body 612 has a base layer 620, a reagent holding layer 630, a channel forming layer 640 with a U-shaped cutout 642, and a cover 650 with an optional inlet notch 654. Base layer 620 has a conductive layer 621 on which is delineated at least five conductive paths 622, 624, 626, 628, and 629. Reagent holding layer 630 has at least five reagent holding openings 632, 634, 636, 638, and 639. Reagent holding opening 632 exposes a portion of conductive path 622; reagent holding opening 634 exposes a portion of conductive path 624; reagent holding opening 636 exposes a portion of conductive path 626; reagent holding opening 638 exposes a portion of conductive path 628; and reagent holding opening 639 exposes a portion of conductive path 629; all forming respective electrode wells.

The five reagent holding openings 632, 634, 636, 638, and 639 define electrode areas W1, W2, R, W3, and B, respectively, and hold chemical reagents forming a first working electrode, a second working electrode, a third working electrode, a reference electrode and a blank electrode. Generally, electrode well W1 is loaded with a BUN reagent mixture; electrode well W2 is loaded with a creatine reagent mixture; electrode well W3 is loaded with a creatinine/creatine reagent mixture; electrode well B is loaded with a blank reagent mixture; and electrode well R is loaded with a reference mixture. For usable compositions of the creatine and creatinine reagent mixtures, please refer to U.S. Pat. No. 6,767,441 which is incorporated herein by reference. The BUN reagent matrix, the blank reagent mixture, and the reference mixture have been disclosed previously.

An alternative embodiment to the embodiment illustrated in FIGS. 7 and 8 has only four electrodes instead of five electrodes. FIG. 9 shows a combination BUN/creatinine sensor 700 with a laminated body 712, a fluid sampling end 714, an electrical contact end 716, and a vent opening 752. Sensor 700 may also include an optional inlet notch 754. Fluid sampling end 714 includes a sample chamber 717 between sample inlet 718 and vent opening 752.

FIG. 10 shows an expanded view of laminated body 712 of the embodiment in FIG. 9. Laminated body 712 has a base layer 720, a reagent holding layer 730, a channel forming layer 740 with a U-shaped cutout 742, and a cover 750 with an optional inlet notch 754. Base layer 720 has a conductive layer 721 on which is delineated to at least four conductive paths 722, 724, 726, and 728. Reagent holding layer 730 has at least four reagent holding openings 732, 734, 736, and 738. Reagent holding opening 732 exposes a portion of conductive path 722; reagent holding opening 734 exposes a portion of conductive path 724; reagent holding opening 736 exposes a portion of conductive path 726; and reagent holding opening 738 exposes a portion of conductive path 728; all forming respective electrode wells.

The four reagent holding openings 732, 734, 736, and 738 define electrode areas W1, W2, R, and W3, respectively, and hold chemical reagents forming a first working electrode, a second working electrode, a third working electrode, and one reference electrode. Generally, electrode well W1 is loaded with a BUN reagent matrix; electrode well W2 is loaded with a creatinine/creatine reagent mixture; electrode well R is loaded with a reference mixture; and electrode well W3 is loaded with a creatine mixture.

Turning now to FIG. 11, there is illustrated another embodiment of the present invention showing a combination of a BUN sensor system and a creatinine sensor system in a side-by-side configuration. FIG. 11 shows a combination BUN/creatinine sensor 800 with a laminated body 812, a fluid sampling end 814, an electrical contact end 816, and a vent opening 852. Sensor 800 may also include an optional inlet notch 854. Fluid sampling end 814 includes a first sample chamber 817a and a second sample chamber 817b between sample inlet 818 and vent opening 852. It should be understood that sample inlet 818 may optionally be two inlets (one for each of the sample chambers) adjacent to each other and that vent opening 852 may also optionally incorporate separate vent openings for each of the fluid sample channels. In the illustrated embodiment, one of the sample chambers incorporates the BUN sensor system and the other sample chamber incorporates the creatinine sensor system.

FIG. 12 shows an expanded view of laminated body 812 of the embodiment in FIG. 11. Laminated body 812 has a base layer 820, a reagent holding layer 830, a chamber forming layer 840 with a fork-shaped cutout 842 having a first leg 842a and a second leg 842b that form sample chambers 817a, 817b, respectively, and a cover 850 with an optional inlet notch 854. Base layer 820 has a conductive layer 821 on which is delineated a plurality of conductive paths 822, 824, 826, 827, 828, and 829.

Reagent holding layer 830 has six reagent holding openings 832, 834, 836, 837, 838, and 839. Reagent holding opening 832 exposes a portion of conductive path 822; reagent holding opening 834 exposes a portion of conductive path 824; reagent holding opening 836 exposes a portion of conductive path 826; reagent holding opening 837 exposes a portion of conductive path 827; reagent holding opening 838 exposes a portion of conductive path 828; and reagent holding opening 839 exposes a portion of conductive path 829; all forming respective electrode reagent wells.

Figure 13:
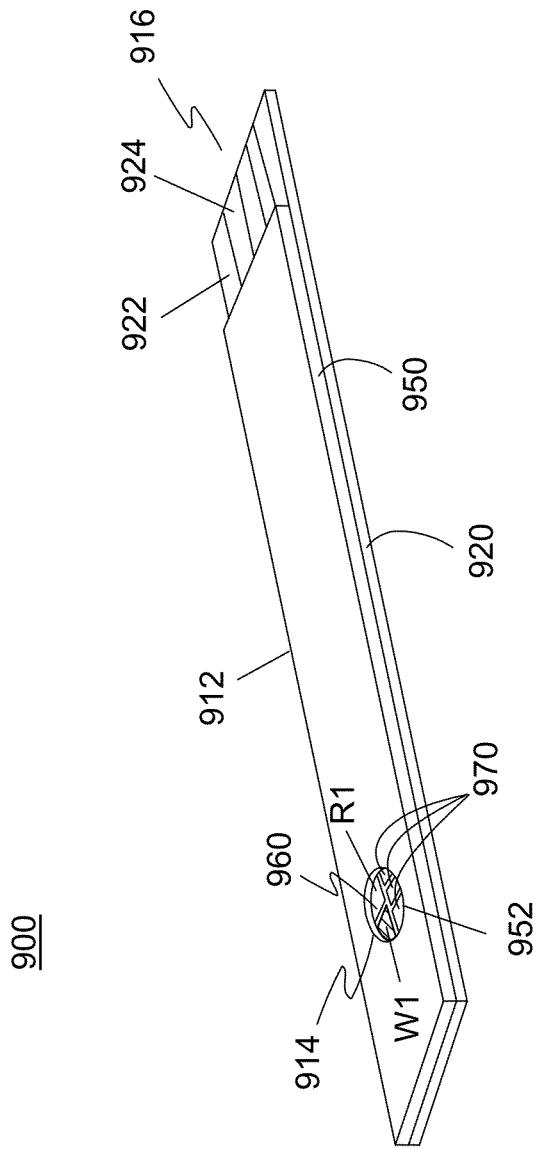
FIG. 13 is a perspective view of another embodiment of the present invention showing the BUN sensor of the present invention.

Turning now to FIG. 13, there is illustrated another embodiment of the present invention showing a basic disposable BUN sensor 900. Disposable sensor 900 has a laminated body 912, a sample receiving well 914 and an electrical contact end 916. Laminated body 912 has a base layer 920 and a cover 950. Cover 950 has a sample opening 952 that forms, when combined with base layer 920, sample receiving well 914. Base layer 920 has at least two electrical paths 922 and 924, which have a first portion exposed at electrical contact end 916 for connection to a meter device (not shown) and a second portion exposed by sample receiving well 914.

Sample receiving well 914 consists of a base and a transverse, circumferential wall extending from the base forming a single structure configured as both a test chamber and a sample inlet. The second portion of electrical paths 922 and 924 exposed by sample receiving well 914 create at least a first working electrode W1 and at least a reference electrode R1. A BUN reagent mixture 960 (represented by the hash marks in the FIG. 13) contains at least urease and is disposed on the first working electrode W1. As previously disclosed, the preferred BUN reagent mixture is reagent mixture 1. The reference electrode R1 may contain any reference material previously disclosed. In this embodiment of the present invention, sample receiving well 914 serves as both the sample inlet and the sample chamber for receiving a fluid sample such as blood for the determination of BUN.

It should be understood that the conduit paths in any of the embodiments disclosed herein may be made from any non-corroding metal. Carbon deposits such as for example carbon paste may also be used as the conduit paths, all as is well known by those of ordinary skill in the art.

Enzymes

The BUN sensor of the present invention includes at least a urea-sensitive enzyme capable of reacting with urea. This enzyme is essential to obtain the electrochemical signal for urea. A commercially available urease such as that available as Cat No. URH-201 from Toyobo, Osaka, Japan may be added into the reagent mixture used for the BUN working electrode. The concentration of urease in the reagent mixture is preferably 0.5% (W/W) to 25%. More preferably, the concentration of urease is about 10%.

Polymers

The polymers used as binders should be sufficiently water-soluble and should also be capable of stabilizing and binding all other chemicals in the reagents in the electrode areas to the conductive surface layer. Preferably, at least two polymers were added in the reagent mixture of the present invention. One of the preferred polymers is polyethylene oxide (PEO). Its molecular weight ranges from thousands to millions. Preferably, the molecular weight is over 1 million. More preferably, the molecular weight is about 4 million. Such a product is available from Scientific Polymer Products, NY, USA (MW 4,000,000, Cat No. 344). The concentration of PEO in the reagent mixture is preferably 0.04% (W/W) to 2%. More preferably, the concentration of PEO is about 0.4%. The other polymer is preferably methylcellulose, which is available under the brand name of Methocel 60 HG (Cat. No. 64655, Fluka Chemicals, Milwaukee, Wis., USA). The concentration of Methocel 60 HG in the reagent mixture is preferably 0.02% (W/W) to 5%. More preferably, the concentration of Methocel 60 HG is about 0.75%.

Surfactants

The surfactant is needed only to facilitate dispensing of the reagent mixture into the openings for the working and reference electrodes, as well as for quickly dissolving the dry chemical reagents when a sample is applied to the channel. The amount and type of surfactant is selected to assure the previously mentioned function and to avoid a denaturing effect on the enzymes. Surfactants can be selected from, but are not limited to, various anionic, cationic, non-ionic and zwitterionic detergents, such as polyoxyethylene ether, Tween 20, sodium cholate hydrate, hexadecylpyridinium cholide monohydrate and CHAPs. The preferred surfactant is a polyoxyethylene ether. More preferably, it is t-octylphenoxypolyethoxyethanol and is available under the brand name Triton X-100. The concentration of Triton X-100 in the reagent mixture is preferably 0.01% (W/W) to 2%. More preferably, the concentration of Triton X-100 is about 0.08%.

The Buffer

Optionally, a buffer may be present along with a redox mediator in dried form in the sensor strip of the present invention. The buffer is present in a sufficient amount so as to substantially maintain the pH of the reagent mixtures. Examples of suitable buffers include citric acid, phosphates, Tris and the like. In the present invention, a concentration range of about 5 mM to 150 mM Tris buffer with a pH of about 8 is employed to prepare the reagent mixtures.

Bulking Reagent

A water soluble and inactive ingredient or bulking agent is preferably added into the reagent mixture, such that the electrode openings will not trap bubbles when a sample fluid fills the capillary channel. Various sugars, such as trehalose, galactose, glucose, sucrose, lactose, mannitol, mannose, fructose, sucrose, lactose, lactitol, sorbitol, xylitol maltose, etc., can be added into the reagent mixture as long as they do not react with other ingredients and are inactive at the electrode surface. The preferred sugar is sorbitol. The concentration of sorbitol in the reagent mixture is preferably 0.5% (W/W) to 25%. More preferably, the concentration of D(+) trehalose is about 10%.

Redox Mediators

The redox mediators are not necessary to obtain the BUN signal for the BUN working electrode. The redox mediators are necessary for the reference electrodes when the preferred reference reagent mixtures are used in order for the reference electrode to function properly. It is desirable that the mediator is stable in the matrix. It is still desirable that the mediator can maintain a desired potential for the BUN working electrode. The mediator can be selected from, but not limited to, various metal complexes and organic redox compounds, such as potassium ferricyanide, ferrocene and its derivatives, promazine, tetrathiafulvalene, methyl blue, 1,4-benzoquinone, 1,4-bis(N,N-dimethylamino)benzene, and 4,4'-dihydrobiphenyl. The preferred mediator in the present invention is an oxidized form, such as potassium ferricyanide ($K_3Fe(CN)_6$). The concentration of potassium ferricyanide in the reagent mixture is preferably 0.5% (W/W) to 15%. More preferably, the concentration of potassium ferricyanide is about 10%. It should be noted that a silver or Ag/AgCl layer or other reference electrode materials can be applied to the reference electrode opening, which do not require the use of an additional redox mediator such as those listed above.

Accordingly, the reagent mixture (referred to below as "reagent mixture 1") used for the BUN working electrode (W) contains 0.75% (W/W) Methocel 60 HG, 0.4% (W/W) polyethylene oxide, 0.08% (W/W) Triton X-100, 10% sorbitol, 5% (W/W) urease and 20 mM Tris buffer (pH 8). The reagent mixture (referred to below as "reagent mixture 2") used for the blank electrode (B) contains 0.75% (W/W) Methocel 60 HG, 0.4% (W/W) polyethylene oxide, 0.08% (W/W) Triton X-100, 10% sorbitol, and 20 mM Tris buffer (pH 8). The reagent mixture (referred to below as "reagent mixture 3") used for the BUN reference electrode contains 0.75% (W/W) Methocel 60 HG, 0.4% (W/W) polyethylene oxide, and 0.08% (W/W) Triton X-100, 10% (W/W) potassium ferricyanide, and 20 mM Tris buffer (pH 8).

Preparation of the Reagent Mixtures

Reagent mixture 1 was preferably prepared in two steps, although it can be prepared in one step:

Step 1: Into 100 ml of 20 mM Tris buffer (pH 8), add 0.75 g Methocel 60 HG, 0.4 g polyethylene oxide, 10.0 gram sorbitol, and 0.08 g Triton X-100. Stir the solution until dissolved.

Step 2: Into the above solution, add 5 g urease. Stir the solution until dissolved. The resulting solution is ready for dispensing.

Reagent mixture 2 was prepared as below:

Into 100 ml of 20 mM Tris buffer (pH 8), add 0.75 g Methocel 60 HG, 0.4 g polyethylene oxide, 10.0 gram sorbitol, and 0.08 g Triton X-100. Stir the solution until dissolved.

Reagent mixture 3 was prepared in two steps:

Step 1: Into 100 ml of 20 mM Tris buffer (pH 8), add 0.75 g Methocel 60 HG, 0.4 g polyethylene oxide, and 0.08 g Triton X-100. Stir the solution until dissolved.

Step 2: Into the above solution, add 10 g potassium ferricyanide. Stir the solution until dissolved. The resulting solution is ready for dispensing.

Sensor/Strip Construction

Assembly of the various embodiments of the present invention is relatively straightforward. Generally for the 4-layer configuration, the base layer and reagent holding layer are laminated to each other followed by dispensing the reagent mixtures into their respective electrode wells. After drying the reagent mixtures, the channel forming layer is laminated onto the reagent holding layer and the cover is then laminated onto the channel forming layer. For the combination sensor construction, the base layer and the reagent holding layer are laminated to each other followed by dispensing the reagent mixtures within their respective electrode wells (or within each of the electrode wells in the legs of the side-by-side embodiment). After drying the reagent mixture, the channel forming layer is laminated onto the reagent holding layer and the cover is then laminated onto the channel forming layer.

More particularly, a piece of a gold polyester film is cut to shape as illustrated in FIG. 2, forming base layer 20 of sensor 10. A laser (previously disclosed) is used to score the gold polyester film. As illustrated in FIG. 2, the film is scored by the laser such that three electrodes at sample fluid end 14 and three contact points 22, 24 and 26 are formed at electrical contact end 16. The scoring line is very thin but sufficient to create three separate electrical paths. A scoring line 28 may optionally be made, but is not necessary, along the outer edge of base layer 20 to avoid potential static problems which could cause a noisy signal from the finished sensor 10.

A piece of one-sided adhesive tape is then cut to size and shape, forming reagent holding layer 30 so that it will cover a major portion of conductive layer 21 of base layer 20 except for exposing a small electrical contact area illustrated in FIG. 1.

Before attaching reagent holding layer 30 to base layer 20, three circular openings 32, 34 and 36 of substantially equal size are punched by laser, or by mechanical means such as a die-punch assembly, creating electrode openings 32, 34 and 36 in reagent holding layer 30. The preferred hole size for opening 32, 34 and 36 has a typical diameter of about 0.030 in. (0.76 mm). As illustrated in FIG. 2, electrode openings 32, 34 and 36 are aligned with each other and have a spacing of about 0.025 in (0.63 mm) between them. The circular openings are for illustrative purposes only. It should be understood that the shape and size of the openings and the distance between the openings are not critical, provided that the size of the openings is big enough to hold sufficient chemical reagents for the electrodes to function properly but small enough to allow for a reasonably small sample chamber. As stated previously, the preferred arrangement of the electrodes formed in openings 32, 34 and 36 is W (working electrode), R (reference electrode) and B (blank electrode). Reagent holding layer 30 is then attached to base layer 20 in such a way as to define the electrode wells W, R and B. A quantity of silver/silver chloride ink is added into electrode well R (opening 34) and then the partially assembled sensor strip is preferably heated/baked at about 50° C. for about 1 hour, forming the reference electrode.

Following creation of the reference electrode, approximately 0.05 to 0.09 μL of reagent mixture 1 is dispensed into electrode area W. As described above, reagent mixture 1 is preferably a mixture of an enzyme, a stabilizer, a binder, a surfactant, and a buffer. Similarly, reagent mixture 2 is dispersed into electrode area B. Reagent mixture 2 is preferably similar to reagent mixture 1 but without the presence of the enzyme urease.

After the addition of the reagents, the reagents are dried. Drying of the reagents can occur within a temperature range of about room temperature to about 60° C. The length of time required to dry the reagents is dependent on the temperature at which the drying process is performed. Drying at a higher temperature for too long a period of time reduces the activity of the enzyme.

It should be understood that if a reference reagent containing a redox mediator/couple is used in place of the silver/silver-chloride ink, the reference reagent may be disposed in the reference well at the same time Reagents 1 and 2 are disposed in the working electrode wells and all three reagents dried simultaneously at the same drying conditions.

After drying, a piece of double-sided tape available from Adhesive Research is fashioned into chamber forming layer 40 containing U-shaped channel 42. Chamber forming layer 40 is then layered onto reagent holding layer 30. As mentioned earlier, this chamber forming layer 40 serves as a spacer and defines the size of the sample chamber 17. Its width and length are optimized to provide for a relatively quick moving fluid sample.

A piece of a transparency film (Cat. No. PP2200 or PP2500 available from 3M) is fashioned into top layer 50. A rectangular vent opening 52 is made using the laser previously mentioned or by means of a die-punch. Vent opening 52 is located approximately 0.180 in. (4.57 mm) from fluid entrance 54. Top layer 50 is aligned and layered onto chamber forming layer 40 to complete the assembly of sensor 10, as illustrated in FIG. 1.

Although the description of electrode construction above describes construction for a single sensor, the design and materials used are ideal for making multiple sensors from one piece of each layer material. This would be accomplished by starting with a relatively large piece of base layer having a conducting layer thereon. A plurality of scored lines are made into the conductive layer such that a repetitive pattern is created using the preferred scribing method previously described, whereby each pattern will eventually define the conductive paths for each sensor. Similarly, a large piece of the reagent holding layer material also having a plurality of openings in a repetitive pattern is sized to fit over the base layer in such a way that a plurality of sensors will be made when completed. The size of each aperture and the electrode material disposed in the plurality of electrode areas W, R and B are similar to that disclosed above. After disposing the reagent mixture in their respective reagent holding openings and drying process, a large piece of the channel forming layer material having a plurality of elongated apertures is layered onto the reagent holding layer material such that each elongated aperture of the channel forming layer material contains corresponding openings of the reagent holding layer material. A comparably-sized cover layer material having a plurality of vent openings and notch-forming openings in a repetitive pattern is layered onto the chamber forming layer material. The laminated sheet is then cut in appropriate locations to form individual urea sensors.

The following examples illustrate the unique features of the present invention. All sensors of the present invention were tested on a breadboard urea meter manufactured by Nova Biomedical Corporation of Waltham, Mass. A potential of approximately 0.80 Volts was applied across the working electrodes and the reference electrode when the reference electrode was a silver/silver-chloride electrode and the resultant current signals were converted to urea concentrations. The readings were compared to readings (control readings) obtained on the same samples using a Vitros® Chemistry System (Model DT 6011, Ortho-Clinical Diagnostic, Rochester, N.Y.).

A potential of approximately 0.4 Volts was applied across the working electrodes and the reference electrodes when the reference electrode was a redox mediator/couple in a reagent matrix and the resultant current signals were converted to urea concentrations. The readings were compared to readings (control readings) obtained on the same samples using a Dimensions® clinical chemistry system (Model RxL, Dade Behring, Inc.).

Example 1

Demonstration of Determination of Urea Concentration with Ag—AgCl Reference

Figure 14:
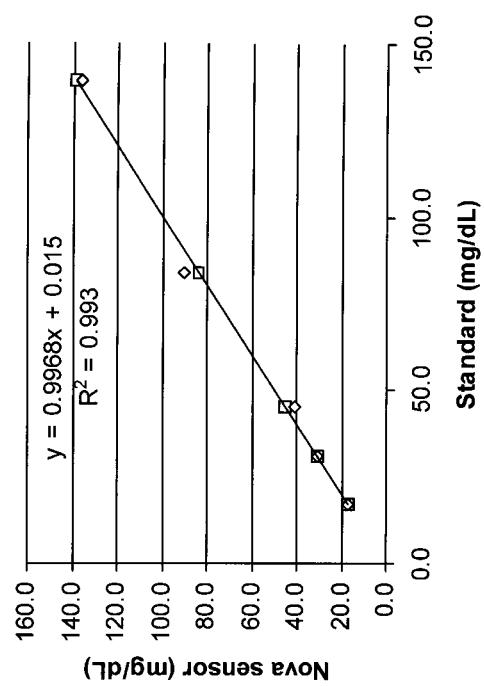
FIG. 14 shows the correlation of the readings obtained using the present invention with a Ag—AgCl reference electrode to readings obtained with an analytical chemistry system.

Blood samples with different urea concentrations were tested with the urea sensors of the present invention having a silver-silver chloride reference electrode and with the Vitros® Chemistry System DT6011 (Ortho-Clinical Diagnostics, Inc., Rochester, N.Y.). FIG. 14 shows the determination of BUN concentration in mg/dL in blood samples using the urea sensors of the present invention to varying urea concentrations in the blood samples. It is noted that these determinations are raw data before any compensation for hematocrit, in order to show the actual correlation of the unmanipulated data.

As seen from the graph, the sensors of the present invention respond to the urea concentration in the blood samples over a tested range of about 17 mg/dL to about 139 mg/dL of blood urea nitrogen. The average coefficient of variation for the sensors of the present invention using a silver/silver-chloride reference electrode is about 4.5%.

Example 2

Demonstration of Determination of Urea Concentration with Redox Reference

Figure 15:
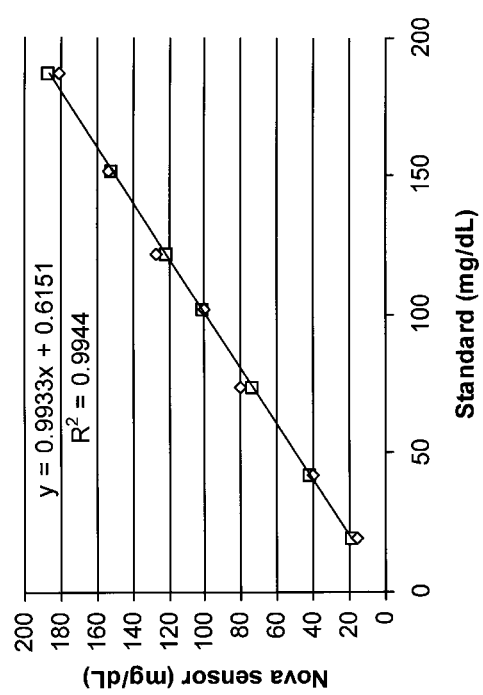
FIG. 15 shows the correlation of the readings obtained using the present invention with a redox mediator-based reference electrode to readings obtained with an analytical chemistry system.

Blood samples with different urea concentrations were tested with the urea sensors of the present invention having a redox mediator/couple reference matrix and with a Dimension® Chemistry System (Dimension RxL, Dade Behring, Inc.). FIG. 15 shows the determination of BUN concentration in mg/dL in blood samples using the urea sensors of the present invention to varying urea concentrations in the blood samples.

As seen from the graph, the sensors of the present invention respond to the urea concentration in the blood samples over a tested range of about 19 mg/dL to about 187 mg/dL of blood urea nitrogen. The average coefficient of variation for the sensors of the present invention having a redox mediator/couple based reference is about 6.4%.

Note that the testing results can be corrected for hematocrit interference. The hematocrit of the blood sample can be calculated based on the impedance measurements between two electrodes, which has been disclosed in the following US published patents and patent applications (U.S. Pat. Nos. 6,767,441; 6,287,451; 6,837,976).

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disposable urea sensor comprising:
   a laminated body having a fluid sample inlet end and an electrical contact end, said laminated body includes a base layer, a reagent holding layer with cutouts defining a working electrode and a reference electrode, a channel forming layer and a cover;
   a fluid sample inlet at said fluid sample inlet end;
   a substantially flat sample chamber in communication between said fluid sample inlet and a vent opening wherein said sample chamber is adapted to collect a fluid sample through said fluid sample inlet, said substantially flat sample chamber defined by said base layer, said reagent holding layer, said channel forming layer and said cover;
   a working electrode and a reference electrode within said sample chamber; and
   a dissolvable mixture of a reagent matrix disposed directly on said working electrode wherein said reagent matrix contains urease but absent any redox mediator and a dissolvable mixture of a reference matrix disposed directly on said reference electrode wherein said reference matrix contains a redox mediator.

2. The sensor of claim 1 wherein said reagent matrix further includes one or more of the materials selected from the group consisting of a binder, a buffer, a surfactant, a stabilizer, and a bulking agent.

3. The sensor of claim 2 wherein said binder is a cellulose material.

4. The sensor of claim 3 wherein said cellulose material is hydroxypropyl cellulose.

5. The sensor of claim 1 further comprising a blank electrode and a second reagent matrix disposed on said blank electrode wherein said second reagent matrix includes a buffer.

* * * * *